United States Patent [19]
Conti-Tronconi et al.

[11] Patent Number: 5,158,884
[45] Date of Patent: Oct. 27, 1992

[54] IMMUNODOMINANT ACETYLCHOLINE RECEPTOR PEPTIDES USEFUL FOR T-HELPER CELL SENSITIZATION

[75] Inventors: Bianca M. Conti-Tronconi; Maria P. Protti, both of Minneapolis, Minn.

[73] Assignee: Regents of the University of Minnesota, Minneapolis, Minn.

[21] Appl. No.: 580,317

[22] Filed: Sep. 10, 1990

[51] Int. Cl.$^5$ .................. C12N 5/00; C12N 5/02; C12N 5/08; C07K 7/08
[52] U.S. Cl. .................. 435/240.2; 435/240.21; 435/240.25; 530/326
[58] Field of Search .................. 435/240.2, 240.21

[56] References Cited

U.S. PATENT DOCUMENTS 4,923,799  5/1990  Mak .................................. 435/6

OTHER PUBLICATIONS

Hohlfield, et al. Amphipathic Segment of the Nicotinic Receptor Alpha Subunit Contains Epitopes Recognized by T Lymphocytes ... J. Clinical Investigation, vol. 81, pp. 657-660 1988.
Harcourt, et al. A Juxta-Membrane Epitope on the Human Acetylcholine Receptor Recognized by T Cells in Myasthenia Gravis J. Clinical Investigation, vol. 82, pp. 1295-1300.
Hohlfield, et al. Anti-Nicotine Receptor Autoimmunity in Myasthenia Gravis Monogr. Allergy, vol. 25, pp. 50-67 1988.
Nelms, et al. Autoimmune T Lymphocytes in Myasthenia Gravis J. Clinical Investigation, vol. 83, pp. 785-790 1989.
M. P. Protti et al., *J. Immunol.*, 144, 1276 (Feb. 1990).
M. Bellone et al., *J. Immunol.*, 143, 3568 (Dec. 1989).
S. Nelson et al., *J. Neuroimmunol.*, 29, 81 (1990).
M. P. Protti et al., *J. Immunol.*, 144, 1711 (1990).
S. J. Tzartos et al., *PNAS USA*, 85, 2899 (1988).
O. Lider et al., *Science*, 239, 181 (1988).
A. A. Vandenberg et al., *Nature*, 341, 541 (1989).
R. Edelson et al., *New England J. Med.*, 316, 297 (1987).
M. Noda et al., *Nature*, 305 818 (1983).
D. Neumann et al., *PNAS USA*, 83, 9250 (1986).
S. Ralston et al., *Biochemistry*, 26, 3261 (1987).
R. Schoepfer et al., *FEBS Letters*, 226, 235 (1988).
I. R. Cohen et al., *Immunology Today*, 9, 11 (1988).
C. A. Janeway, *Nature*, 341, 482 (1989).
L. Steinman et al., *The FASEB J.*, 4, 2726 (1990).

*Primary Examiner*—John J. Doll
*Assistant Examiner*—George C. Elliott
*Attorney, Agent, or Firm*—Merchant, Gould, Smith, Edell, Welter & Schmidt

[57] ABSTRACT

The present invention provides four synthetic peptides corresponding to subunits of the α-subunit of the nicotinic acetyl choline receptor (AChR) which have formulas (1-4):

(1) gln-il e-val-thr-thr-asn-val-arg-leu-lys-gln-gln-trp-val-asp-tyr-asn-leu-lys-trp;
(2) ala-ile-val-lys-phe-thr-lys-val-leu-leu-gln-tyr-thr-gly-his-ile-thr-trp-thr-pro;
(3) ser-thr-his-val-met-pro-asn-trp-val-arg-lys-val-phe-ile-asp-thr-ile-pro-asn; and
(4) ile-ile-gly-thr-leu-ala-val-phe-ala-gly-arg-leu-ile-glu-leu-asn-gln-gln-gly;

as well as biologically active fragments thereof, and anti-AChR T-helper cell populations having receptor sites therefor.

3 Claims, 1 Drawing Sheet

IMMUNODOMINANT ACETYLCHOLINE RECEPTOR PEPTIDES USEFUL FOR T-HELPER CELL SENSITIZATION

BACKGROUND OF THE INVENTION

This invention was made with the support of NIH grant number 2R01-NS23919. The U.S. government has certain rights in the invention.

A. The Immune Response

The capacity to respond to immunologic stimuli resides primarily in the cells of the lymphoid system. During embryonic life, a stem cell develops, which differentiates along several different lines. For example, the stem cell may turn into a lymphoid stem cell which may differentiate to form at least two distinct lymphocyte populations. One population, called T lymphocytes, is the effector agent in cell-mediated immunity, while the other (B lymphocytes) is the primary effector of antibody-controlled, or humoral immunity. The stimulus for B cell antibody production is the attachment of an antigen (Ag) to B-cell surface immunoglobulin. Thus, B cell populations are largely responsible for specific antibody (Ab) production in the host. At times, and for certain Ags, B cells require the cooperation of T cells for effective Ab production.

Of the classes of T lymphocytes, T helper ($T_H$) cells are antigen-specific cells that are involved in primary immune recognition and host defense reactions against bacterial, viral, fungal and other antigens. The T cytotoxic ($T_c$) cells are antigen-specific effector cells which can kill target cells following their infection by pathological agents.

While T helper ($T_H$) cells are antigen-specific, they cannot recognize free antigen. For recognition and subsequent $T_H$ cell activation and proliferation to occur, the antigen must be presented to receptors or a receptor complex on the $T_H$ cell together with major histocompatibility complex (MHC) class II products. Thus, $T_H$ cell recognition of a pathogenic antigen is MHC class II "restricted" in that a given population of $T_H$ cells must be either autologous or share one or more MHC class II products expressed by the host. Likewise, $T_c$ cells recognize Ag in association with class I MHC products.

In the case of $T_H$ cells, this function is performed by a limited number of specialized cells termed "antigen-presenting cells" (APC). It is now well-established that T helper ($T_H$) cells recognize processed soluble antigen in association with class II MHC product, expressed on the surface of macrophages. Recently, other cell types such as resting and activated B cells, dendritic cells, epidermal Langerhans' cells and human dermal fibroblasts, have also been shown to present antigen to T cells.

If a given $T_H$ cell possesses receptors or a receptor complex which enable it to recognize a given MHC-class II product-antigen complex, it becomes activated, proliferates and generates lymphokines such as interleukin 2 (IL-2). The lymphokines in turn cause the proliferation of several types of "killer cells", including $T_c$ cells and macrophages, which can exhibit antimicrobial and tumoricidal activity. After stimulation subsides, survivors of the expanded $T_H$ cells remain as member cells in the body, and can expand rapidly again when the same antigen is presented.

Numerous attempts have been made to isolate and maintain homogenous populations of $T_c$ or $T_H$ cells and to characterize them in terms of their antigen specificity and MHC restriction. These attempts usually involve the stimulation of mononuclear cells from a seropositive human or murine host with antigenic bacterial or viral preparations in combination with non-proliferative APCs, such as irradiated autologous mononuclear cells (MNCs). Proliferating polyclonal populations of $T_H$ cells or $T_c$ cells can be cloned by limiting dilution to obtain homogenous populations and then further proliferated and characterized by a variety of techniques. As noted by Rosenberg et al., in *New England J. Med.*, 313, 1485 (1985), in the case of cloned LAK cells, one of the major obstacles in cloning T lymphocytes is the limited availability of autologous, or alternatively, allogeneic MHC LA-matched MNCs, especially from clinical subjects.

To overcome this problem, APCs other than autologous MNCs have been employed as APCs. For example, T. Issukutz et al., *J. Immunol.*, 129, 1446 (1982) first disclosed that autologous Epstein-Barr virus (EBV)-transformed LCL lines can present antigens associated with tetanus toxoid to tetanus-reactive polyclonal T cells and T cell clones. D. R. Kaplan et al., in *Cellular Immunology*, 88, 193 (1984) reported the production of three $T_c$ cell clones by the proliferation of peripheral blood MNCs from a type A influenza immune donor. One of the clones proliferated in the presence of irradiated, virus-infected, autologous MNCs or in the presence of irradiated, infected Epstein-Barr virus transformed allogeneic lymphoblastoid cells (LCL). B. G. Elferink et al., *Scand J. Immunol.*, 22, 585 (1985) further showed that autologous and allogenic Epstein-Barr Virus (EBV)-transformed LCL lines can present antigens associated with *M. leprae* bacilli to *M. leprae*-reactive cloned T cell lines.

B. Myasthenia Gravis

Myasthenia gravis ("MG") is a human paralysis due to an autoimmune response against the nicotinic acetylcholine receptor (AChR) at the neuromuscular junction [J. Linstrom, *Ann. Rev. of Immunol.*, 3, 109 (1985).] Anti-AChR antibodies cause accelerated destruction and functional impairment of the AChR and failure of neuromuscular transmission. The autoantibody response to AChR is regulated and probably initiated by activated T helper cells that have escaped from their physiological state of tolerance to this self-constituent. T helper cells specific to AChR are activated when their antigen-specific T cell receptors (TcR) recognize a complex formed between epitopes on AChR and class II molecules of the MHC. The activated $T_H$ cells may then interact with AChR specific B lymphocytes, resulting in the production of pathogenic anti-AChR antibodies.

The AChR consists of four subunit polypeptides ($\alpha$, $\beta$, $\gamma$ and $\delta$) [M. P. McCarthy et al., *Ann. Rev. Neurosci.*, 9, 383 (1986).] The anti-AChR antibodies found in MG patients are mostly directed against a small area of the AChR $\alpha$ subunit, called Main Immunogenic Region (MIR). However, little is known about the induction and control of the anti-AChR antibody response.

Anti-AChR specific T-helper ($T_H$) CD4+ cells exist in the blood and the thyroid gland of myasthenic patients and $T_H$ cell lines specific for the AChR have been propagated in vitro from both of these sources. These $T_H$ cell lines recognize the AChR in class II restricted fashion [R. Hohlfeld et al., *J. Immunol.*, 135, 2393 (1985); R. Hohlfeld et al., *PNAS USA*, 84, 5379 (1982)].

Because large amounts of Torpedo (electric ray) AChR (TAChR) can be readily isolated, this receptor has been used to study the T cell response to the AChR in MG and to propagate the AChR-specific $T_H$ cell lines [R. Hohlfeld et al., *PNAS USA*, 84, 5379 (1987); R. Hohlfeld et al., *Neurology*. 36, 618 (1986).]Propagation of $T_H$ cells with TAChR has two disadvantages. First, because of the sequence differences between Torpedo and human AChR, the T cell clones that recognize sequence segments which are nonconserved between human and TAChR are lost during the propagation process. Second, a limited number of T cells are obtained, perhaps because of clonal loss, and large scale testing of these T cell lines for epitope localization is not feasible. Human AChR is the Ag of choice to study the autoimmune responses in MG. Unfortunately, this AChR can be obtained only in minute amounts from muscle of amputated legs.

Therefore, there is a need for synthetic polypeptides which correspond to specific segments of AChR, and which can be used to propagate polyclonal and monoclonal $T_H$ cell lines from MG patients. In turn, these $T_H$ cell lines would be useful to determine, in vitro, which parts of the AChR molecule are involved in the induction of this autoreactive $T_H$ sensitization and how such epitopes are recognized in this complex interaction between the class II-restricting elements and the specific TcR. Furthermore, AChR-specific autoreactive $T_H$ lines from MG patients would be useful intermediates in the development of specific immunosuppressive MG therapies.

SUMMARY OF THE INVENTION

The present invention provides four synthetic peptides comprising the following amino acid sequences (1–4):

(1)  gln-ile-val-thr-thr-asn-val-arg-leu-lys-gln-gln-trp-val-asp-tyr-asn-leu-lys-trp;

(2)  ala-ile-val-lys-phe-thr-lys-val-leu-leu-gln-tyr-thr-gly-his-ile-thr-trp-thr-pro;

(3)  ser-thr-his-val-met-pro-asn-trp-val-arg-lys-val-phe-ile-asp-thr-ile-pro-asn; and (4)  ile-ile-gly-thr-leu-ala-val-phe-ala-gly-arg-leu-ile-glu-leu-asn-gln-gln-gly.

These peptides are depicted conventionally, from the amino terminus (left end) to the carboxyl terminus (right end), and formally represent amino acid residues 48–67 (1); 101–120 (2); 304–322 (3) and 419–437 (4) of the human α subunit of AChR [M. Noda et al., *Nature*, 305, 818 (1983); R.M. Schoepfer et al., *FEBS Lett.*, 226, 235 (1981).]The single letter codes for these peptides are: (1) QIVTTNVRLKQQWVDYNLKW; (2) AIVKFTKVLLQYTGHITWTP; (3) STHVMPNWVRKVFIDTIPN; and (4) IIGTLAVFAGRLIELNQQG.

These peptides each can stimulate the proliferation of anti-AChR $T_H$ cell lines derived from myasthenic patients, irrespective of the HLA-type of the patient, as determined by a known proliferation assay [See M. P. Protti et al., *J. Immunol.*, 144, 1711 (1990).]The polypeptides do not stimulate the proliferation of $T_H$ cell lines when peripheral blood mononucleocytes from normal subjects are exposed thereto. Peptides 1–4 do not correspond to α-subunit sequences known to form the MIR or the cholinergic binding site. Therefore, the present invention also provides an essentially pure population of polyclonal or monoclonal CD3[30], CD4+, CD8− $T_H$ cells obtained from myasthenic patients, which cells have a receptor for, and can proliferate when exposed to, peptides 1–4.

The use of peptides 1–4 to prepare AChR-specific $T_H$ cell lines is an improvement over the use of TAChR, which contains non-conserved sequences and yields only limited number of T cells. Peptides 1–4 can be prepared in large quantities and in high purity by chemical synthesis and thus are much less expensive and more readily quantified than is tissue-derived human AChR.

Because T epitopes can be as small as 5 amino acid residues, peptides 1–4 may each contain a single smaller immunodominant epitope which is recognized within any MHC-class II haplotype. Such an immunodominant epitope would be the $T_H$ cell counterpart of the MIR, which is responsible for the antibody (Ab) response to the AChR, irrespective of the HLA-haplotype of the patients. Therefore, biologically active fragments of peptides 1–4 of at least 7 consecutive amino acid residues are also within the scope of the present invention, wherein the term "biologically-active" is defined to mean that said fragments can also stimulate proliferation of AChR-specific $T_H$ cell lines derived from myasthenic patients.

The presence of a relatively small number of immunodominant epitopes within the α-subunit indicates that the pathogenic T cell receptors involved in epitope recognition are highly restricted. The availability of the $T_H$ cell lines of the invention should permit the identification of the TcR genes and their gene products that are involved in recognition of the immunodominant regions of human AChR.

Treatment with antibody to the TcR gene product, or with the gene product itself, may be an effective treatment to abolish or limit the $T_H$ cell response to human AChR, and thus to block or to alleviate the deleterious effects of MG. For example, vaccination of MG patients with inactivated $T_H$ cells of the present invention, or with isolated TcRs, may give rise to an Ab or T cell response which can block the pathogenic $T_H$ cell response to endogenous AChR. [See D.W. Wraith, *Cell*, 57, 709 (1989); M.B. Feinberg et al., *Cell*, 45, 807, (1986); A.D. Frankel et al., *Science*, 240, 70 (1988).]

Techniques to practice this therapeutic method are generally disclosed by A. A. Vandenbark et al., *Nature*, 341, 541 (Oct. 12, 1989), wherein immunization with both inactivated auto-antigen specific $T_H$ cells and with a synthetic T-cell receptor V-region peptide protected rats against experimentally-induced autoimmune encephalomyelitis, by giving rise to protective V-region peptide-specific T cells. The $T_H$ cells of the present invention can be rendered avirulent by irradiation, by hydrostatic pressure or by chemical crosslinkers such as psoralins. A. BenNun et al., *Nature*, 292, 60 (1981); O. Lider et al., *Ann NYAS*, 457, 267 (1987); O. Linder et al., *PNAS USA*, 84, 4577 (1987); O. Linder, *Science*, 239, 182 (1988); R. Edelson et al., *N. Engl. J. Med.*, 316, 297 (1987).

DETAILED DESCRIPTION OF THE INVENTION

Figure 1:
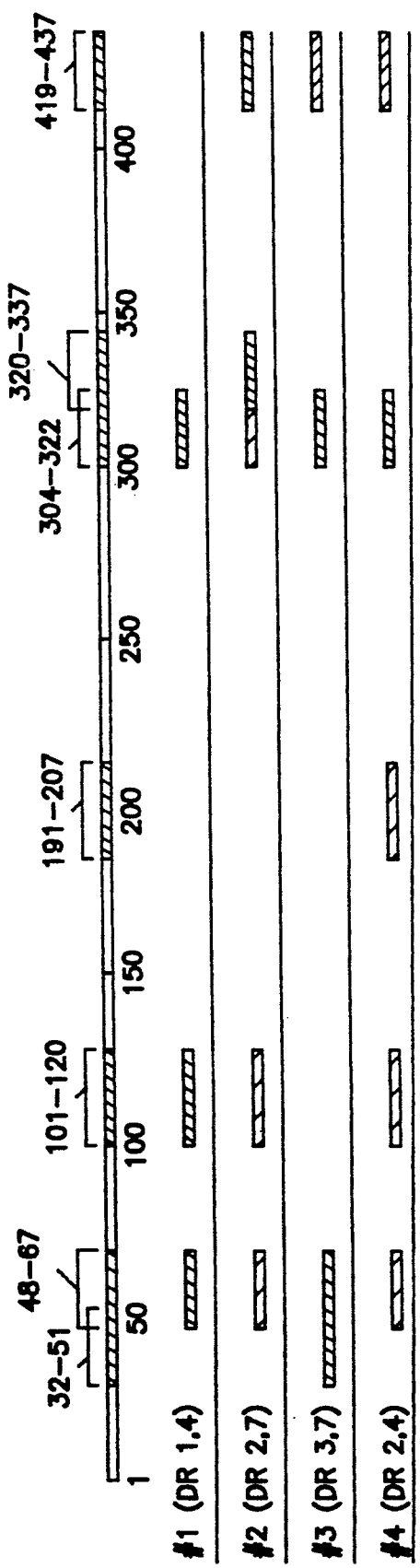
FIG. 1 is a schematic depiction of the peptides recognized by the four T-cell lines and their HLA-DR haplotypes. Peptides which elicited a strong response are indicated as dense hatched segments, peptides which elicited a lower response are indicated as light hatched segments.

The invention will be further described by reference to the following detailed examples wherein the following abbreviations are employed:

α-BGT, α-Bungarotoxin; $^{125}$I-α-BGT, radiolabelled α-Bungarotoxin; AChR, Nicotinic Acetylcholine Receptor; TAChR, Torpedo AChR; MG, Myasthenia Gravis; α Pool, pool of synthetic peptides corresponding to the complete sequence of the α subunit of human muscle AChR; FACS, Fluorescence Activated Cell Sorter; HPLC, High Performance Liquid Chromatography; PBMC, Peripheral blood mononucleocytes; TCM, Tissue Culture Medium; TCGF, T Cell Growth Factor; APC, Antigen Presenting Cells; and PHA, Phytohaemagglutinin.

EXAMPLE I PREPARATION OF T-HELPER CELL LINES

A. Materials and Methods

1. Patients

Anti-AChR CD4+ T-cell polyclonal lines were propagated from the blood of four MG patients. Three patients (#1, #2 and #3) had moderate generalized symptoms, one (#4) was in clinical remission. The HLA type of the patients, as determined by standard microlymphotoxicity techniques was: Patient #1: A2.,AW30/B13,B27/CW1/DR1,DR4/DQ1,DQ3, Patient #2: A2,A29/B7,BW44/DR2,DR7/DQ1,DQ2; Patient #3: A1,A29/B8,BW44/DR3,DR7/DQ2,DQ2; Patient #4: A1/B7,BW44/DR2,DR4/D1Q,DQ3 (NIH Transplantation and Immunology Branch Staff. N/A lymphocyte microcytotoxicity technique rag 39, in *Manual of Tissue Typing Techniques*, T. Ray, ed., NIH publication no. 80-545, USDHEW (1979)).

2. Peptide synthesis and characterization

Thirty-two peptides, 14-20 residues long and corresponding to the complete sequence of the human AChR α subunit were synthesized by manual parallel synthesis according to R.A. Houghten, *PNAS USA*, 82, 5131 (1985). The peptides overlapped each other by 4-8 residues, to minimize the risk of missing epitopes "split" between peptides. The purity of the synthetic peptides was assessed by reversed phase high performance liquid chromatography (HPLC) using a C18 column (Ultrasphere ODS) and a gradient of acetonitrile in 0.1% trifluoroacetic acid in water, which consistently revealed the presence of one main peak of optical density. The composition of the peptides, determined by phenylthiocarbamyl derivitization of the amino acids released by acid hydrolysis, yielded a satisfactory correspondence between experimental and expected values for all peptides, as determined by the methodology of R.L. Heinikson et al., *Anal. Biochem.*, 136, (1984). The sequence and the purity of some randomly selected peptides was further verified by gas-phase sequencing (Applied Biosystems, Foster City, Calif.). Only the expected sequence was found. Contaminating sequences (shorter homologous peptides where one or more residues were randomly missing because of incomplete coupling) were 5-15% of the total signal. The peptides corresponded to the following sequence segments of the α-subunit of AChR: residues 1-14, 7-22, 19-34, 32-51, 48-67, 63-80, 76-93, 89-105, 101-120, 118-137, 135-154, 151-168, 166-185, 181-195, 191-207, 203-218, 214-234, 230-249, 246-264, 261-280, 280-297, 293-308, 304-322, 320-337, 329-347, 343-356, 352-368, 364-380, 376-393, 387-405, 403-421, and 419-437 (end), as numbered by M. Noda et al., *Nature*, 305, 818 (1983) and R.M. Schoepfer et al., *FEBS Lett.*, 226, 235 (1988).

3. Purification and characterization of Torpedo AChR (TAChR)

Native, membrane bound TAChR was prepared from Torpedo californica (J.S. Elliot et al., *PNAS USA*, 76, 2576 (1979)). TAChR concentration was measured as $^{125}$-α-bungarotoxin (α-BGT) binding sites using the disk assay of Schmidt and Raftery, *Anal. Biochem.*, 52, 349 (1973). The specific activity of these preparations (expressed as nmol of $^{125}$I-α-BGT binding sites/mg of protein) was 4-7 nmol/mg of protein (maximum theoretical activity of pure AChR: 7.2 nmol/mg). α-BGT was purified from *Bungarus multicinctus* venom and radiolabelled with $^{125}$I as described by D.G. Clark et al., *Biochemistry*, 11, 1662 (1972) and J. Lindstrom et al., *Meth. Enzymol.*, 74, 432 (1981). The specific activity of $^{125}$I-α-BGT was determined as described by S.G. Blanchard et al., *Biochemistry*, 18, 1875 (1979).

4. Propagation of $T_H$ cell lines specific for the AChR α subunit

The pool of 32 synthetic peptides corresponding to the complete sequence of the α subunit of the human AChR (α Pool) was used to propagate AChR-specific T-cell lines. PBMC (2-4×10$^7$) in RPMI 1640 medium (Gibco) supplemented with 10% heat inactivated human serum, 2 mM L-glutamine, 100 U/ml penicillin, 50 μg/ml streptomycin (Tissue Culture Medium, TCM) containing a final concentration of α Pool of one μg/ml of each peptide, were seeded at a concentration of 1-2×10$^7$/ml in flasks and cultivated for one week. The reactive lymphoblasts were isolated on Percoll gradients as described by J.T. Kurnick et al., *Scand. J. Immunol.*, 10, 563 (1979), further expanded in T-cell growth factor (TCGF) (Lymphocult, Biotest Diagnostics Inc.) containing 10 U/ml of interleukin 2, and enriched by approximately weekly stimulation with the same amount of antigen plus irradiated (4000 rad) autologous or HLA-DR matched PBMC as antigen presenting cells (APC). The four T-cell lines obtained were tested approximately every week for their ability to respond to the α Pool and to PHA. The enrichment in α Pool reactivity was considered satisfactory when the response to the α Pool was comparable or higher than the response to PHA, and this was achieved after 4-9 weeks of culture. The phenotype of the T-cell lines was determined by fluorescence activated cell sorting (FACS) using phycoerythrin conjugated Leu 2 (anti-CD8), Leu 3 (anti-CD4) and Leu 4 (anti-CD3) antibodies. Dilutions, washings and incubations were performed in PBS at 4° C.

5. Microproliferation assay

The resultant T line cells (blasts) were diluted to 2×10$^5$/ml in TCM. Autologous or HLA-DR matched PBMC, to be used as APC, were irradiated (4000 rad) and diluted to 2×10$^6$ in TCM. The cells were plated in triplicate in 96 round bottom well plates (100 μl of blast cells and 100 μl of APC). The cells were stimulated with α-Pool (0.05, 0.1, 0.5, 1 and 5 μg/ml of each peptide), phytohaemoagglutin (1%)(PHA, Wellcome), TCGF (Lymphocult, Biotest Diagnostic, Inc., final concentration of interleukin 2, 10 U/ml) and TAChR (20, 10, 5 and 2.5 μg/ml) and each of the 32 peptides present in the α Pool (10 μg/ml). Triplicate wells with blasts alone and 3 wells with blasts plus APC were used as controls. After 3 days, the cultures were pulsed for 16 hours with $^3$H-thymidine (1 μC/well, specific activity = 6.7 C/mmol, Amersham). The cells were collected with a Skatron Titertek multiple harvester and the thymidine incorporated was measured in a liquid scintillation counter.

B. Results

1. Reactivity of T Cell lines to α-Pool

Four $T_h$ cell lines could be propagated by cycles of stimulation with α-Pool and interleukin 2 for several months. Their phenotype was uniformly CD3+, CD4+, CD8−. The specificity for the α-Pool of the lines was tested by microproliferation assay every week during their propagation. All the lines responded vigorously to the α-Pool. Three lines were tested for cross-reactivity with native TAChR. Two of the (#1 and #4) had a weak but consistent response to TAChR. Line #3 did not cross-react with TAChR. Because the sequences of TAChR and human AChR α subunits are only 81% identical, a limited cross-reactivity of our lines should be expected. In most experiments the anti-AChR $T_H$-cell lines increased their rate of proliferation somewhat when autologous or DR-matched irradiated antigen presenting cells (APC) were added, in the absence of AChR antigens. This may be due to a reaction to the autologous DR molecules, as described for human and rodent T-cells.

Because an in vitro immunization against the α-Pool cannot be excluded, and to investigate whether anti-AChR T-cells are present in the blood of normal subjects, propagation of $T_H$-cell lines was attempted using blood from four healthy subjects using the same procedure as for the myasthenic patients, or by cycles of stimulation with APC alone followed by expansion with IL2. Control $T_H$-Cells could not be propagated for more than two stimulation cycles. The cells obtained responded strongly to APC but they did not respond to the α-Pool or to TAChR.

2. Reactivity of T-cell lines to Individual Peptides

The reactivity of the anti-AChR CD4+ $T_H$-cell lines from myasthenic patients to the individual peptides was periodically investigated by microproliferation assays. The first test was carried out after a satisfactory enrichment in α-Pool specific T-cells was reached, as indicated by reactivity of the α-Pool as high or higher than the response to the specific stimulant phytohaemoagglutin. The basal rate of cell division varied with different lines and even for the same cell line, because it depends on both the anti-DR component of the cell line and the degree to which the T-cells had reverted to the resting state at the time of the test.

A few of the peptides were clearly and consistently recognized. Line #1 in all tests responded to peptides corresponding to human α-subunit residues 48–67, 101–120, and 304–322. Line #2 clearly recognized peptides 320–337 and 419–437. A significant although sometimes smaller response to peptide 48–67, 101–120 and 304–322 was detected in at least one experiment. Line #3 recognized consistently and strongly the two overlapping peptides 32–51, 48–67 and peptide 304–322. In one experiment peptides 419–437 were also recognized. Line #4 strongly recognized peptide 304–322. Peptides 48–67, 101–120, 191–207 and 419–437 were frequently recognized, particularly at the beginning of the propagation of the CD4+ T-cell line. At later stages of propagation these peptides were less frequently recognized, possibly because of clonal loss. CD4+ T-cells which could be propagated for short times from healthy controls by stimulation with APC and α-Pool or APC alone were tested for reactivity to the individual peptides. No response was detected.

FIG. 1 summarizes the α-subunit sequence segments recognized by the four CD4+ lines. Peptides 48–67, 101–120, 304–322 and 419–437 comprise immunodominant regions that are recognized by the autoimmune anti-AChR CD4+ cells of most or all myasthenic patients, irrespective of their HLA-type. Because T epitopes can be as small as 7 residues these peptides, which are twenty or more residue long, may accommodate several overlapping T epitopes, recognized in association with the same or different restriction elements. The $T_H$ immunodominance of these regions may be due to easier cleavage and processing and/or better ability of the excised segments to fold into a secondary structure agreeable with DR molecule binding. Alternatively, one or more of these peptide segments may contain a single immunodominant T epitope, recognized within several or any MHC-class II haplotype. Such an immunodominant epitope would be the $T_H$-cell counterpart of the MIR, which dominates the antibody response to the AChR, irrespective of the HLA-haplotype of the patients. However, none of the these T-immunodominant regions overlaps the MIR, which is between residue 67–76. Likewise, the main constituent loop of the cholinergic binding site, against which antibodies can be produced in myasthenic patients, is within the sequences 184–198.

All of the patents and publications cited hereinabove are hereby incorporated by reference.

The invention has been described with reference to various specific and preferred embodiments and techniques. However, it should be understood that many variations and modifications may be made while remaining within the spirit and scope of the invention.

SEQUENCE LISTING (1) General Information
- (i) Applicant: Conti-Tronconi, Bianca M.
  Protti, Maria P.
- (ii) Title of Invention: Immunodominant Acetylcholine Receptor Peptides Useful for T-Helper Cell Sensitization
- (iii) Number of Sequences: 4
- (iv) Correspondence Address:
  - (A) Addressee: Merchant & Gould
  - (B) Street: 3100 Norwest Center
  - (C) City: Minneapolis
  - (D) State: Minnesota
  - (E) Country: USA
  - (F) Zip Code: 55402
- (v) Computer Readable Form:
  - (A) Medium Type: Diskette, 5.25, 3.5 inch, 20 Mb. storage
  - (B) Computer: Northgate 386
  - (C) Operating System: DOS 4.0
  - (D) Software: WordPerfect ® 5.0
- (vi) Attorney Information:
  - (A) Woessner, Warren D.
  - (B) Registration Number: 30,440
  - (C) Docket No.: 600.206-US-01
- (vii) Telecommunication Information:
  - (A) Telephone: (612) 322-5300
  - (B) Telefax: (612) 322-9081

(2) Information for Sequence ID No. 1:
- (i) Sequence Characteristics
  - (A) Length: 20 amino acid residues
  - (B) Type: Amino acid
  - (C) Topology: Linear
- (ii) Molecule Type: Peptide
- (iii) Fragment Type: Internal fragment

SEQUENCE LISTING (iv) Feature:
 (A) Name/key: fragment of α-subunit of human nicotinic acetylcholine receptor complex
 (B) Location: 48-67
(v) Sequence Description: SEQ ID NO:1:
 Gln Ile Val Thr Thr Asn Val Arg Leu Lys Gln Gln
  53                              58
 Trp Val Asp Tyr Asn Leu Lys Trp
  63                  67

(3) Information for Sequence ID No. 2:
 (i) Sequence Characteristics
  (A) Length: 20 amino acid residues
  (B) Type: Amino acid
  (C) Topology: Linear
 (ii) Molecule Type: Peptide
 (iii) Fragment Type: Internal Fragment
 (iv) Feature:
  (A) Name/Key: Fragment of α-subunit of human nicotinic acetyl choline receptor complex.
  (B) Location: 101-120
 (v) Sequence Description: SEQ ID NO: 2:
  Ala Ile Val Lys Phe Thr Lys Val Leu Leu Gln
  101                             106            111
  Tyr Thr Gly His Ile Thr Trp Thr Pro
                   116             120

(4) Information for Sequence ID NO: 3:
 (i) Sequence Characteristics
  (A) Length: 19 amino acid residues
  (B) Type: Amino acid
  (C) Topology: Linear
 (ii) Molecule Type: Peptide
 (iii) Fragment Type: Internal Fragment
 (iv) Feature:
  (A) Name/Key: Fragment of α-subunit of human nicotinic acetyl choline receptor complex.
  (B) Location 304-322
 (v) Sequence Description: SEQ ID NO: 3:

SEQUENCE LISTING

Ser Thr His Val Met Pro Asn Trp Val Arg Lys
 304                  308                      314
 Val Phe Ile Asp Thr Ile Pro Asn
                 319             322

(4) Information for Sequence ID NO. 4:
 (i) Sequence Characteristics
  (A) Length: 19 amino acid residues
  (B) Type: Amino acid
  (C) Topology: Linear
 (ii) Molecule Type: Peptide
 (iii) Fragment Type: C-terminal Fragment
 (iv) Feature:
  (A) Name/Key: Fragment of α-subunit of nicotinic acetyl choline receptor complex.
  (B) Location: 419-437
 (v) Sequence Description: SEQ ID NO: 4:
  Ile Ile Gly Thr Leu Ala Val Phe Ala Gly Arg
  419                     424                      429
  Leu Ile Glu Leu Asn Gln Gln Gly
                  434             437

What is claimed is:

1. An essentially pure population of human T-helper ($T_H$) cells having a receptor site for at least one synthetic peptide selected from the group consisting of:
 (1) gln-ile-val-thr-thr-asn-val-arg-leu-lys-gln-gln-trp-val-asp-tyr-asn-leu-lys-trp;
 (2) ala-ile-val-lys-phe-thr-lys-val-leu-leu-gln-tyr-thr-gly-his-ile-thr-trp-thr-pro;
 (3) ser-thr-his-val-met-pro-asn-trp-val-arg-lys-val-phe-ile-asp-thr-ile-pro-asn;
 (4) ile-ile-gly-thr-leu-ala-val-phe-ala-gly-arg-leu-ile-glu-leu-asn-gln-gln-gly; and
a fragment of one of said peptides (1-4) having at least five amino acid residues.

2. The T-helper cell population of claim 1 which is polyclonal.

3. The T-helper cell population of claim 1 which is monoclonal.

* * * * *